(12) United States Patent
Har-Shai et al.

(10) Patent No.: US 6,503,246 B1
(45) Date of Patent: Jan. 7, 2003

(54) CRYOPROBE AND METHOD OF TREATING SCARS

(75) Inventors: Yaron Har-Shai, Haifa (IL); Micha Amar, Karmiel (IL)

(73) Assignees: Mor Research Applications Ltd., Petach Tikva (IL); Cleanetica Ltd., Haifa (IL)

( * ) Notice: Subject to any disclaimer, the term of this patent is extended or adjusted under 35 U.S.C. 154(b) by 144 days.

(21) Appl. No.: 09/610,488

(22) Filed: Jul. 5, 2000

(51) Int. Cl.$^7$ ............................................... A61B 18/18
(52) U.S. Cl. ........................................... 606/23; 606/21
(58) Field of Search ............... 606/20–26; 128/DIG. 27

(56) References Cited

U.S. PATENT DOCUMENTS

| | | | | |
|---|---|---|---|---|
| 2,672,032 A | * | 3/1954 | Towse | 165/142 |
| 3,662,755 A | * | 5/1972 | Rautenbach et al. | 606/24 |
| 4,207,897 A | * | 6/1980 | Lloyd et al. | 128/DIG. 27 |
| 4,802,475 A | * | 2/1989 | Weshahy | 128/DIG. 27 |
| 5,254,116 A | | 10/1993 | Baust et al. | |
| 5,906,612 A | | 5/1999 | Chinn | |
| 5,993,444 A | * | 11/1999 | Ammar et al. | 606/21 |
| 6,039,730 A | | 3/2000 | Rabin et al. | |

FOREIGN PATENT DOCUMENTS

GB  2289412 A   11/1995
WO  WO 93/08751   5/1993

OTHER PUBLICATIONS

Zouboulis, C., et al, "Cryosurgical Treatment" *Surgival Techniques for Cutanious Scar Revision*, Ed M. Harahap, New York: Marcel Dekker, Inc. (2000) 185–234.

Weshay, A.H.G., "Intralesional Cryosurgery, a New Technique Using Cryoneedles" *J Dermatol Surg Oncol* 1993; 19:123–126.

Muti, E., et al., "Cryotherapy In The Treatment of Keloid" *Annals of Plastic Surgery* (1983) 11:227–232.

* cited by examiner

*Primary Examiner*—Michael Peffley
(74) *Attorney, Agent, or Firm*—Gary M. Nath; Todd L. Juneau; Sheldon M. McGee

(57) ABSTRACT

An intralesional method for treating a hypertrophic scar or keloid using a cryoprobe. The method comprises: (a) inserting the cryoprobe into the hypertrophic scar or keloid so that the cryoprobe is positioned within the hypertrophic scar or keloid; and (b) introducing a cryogen into the cryoprobe thereby freezing the hypertrophic scar or keloid. The cryoprobe has a sealed distal end comprising a cutting tip. Also disclosed is a cryoprobe comprising an elongated, uninsulated housing having a sealed distal end and a proximal end. The housing comprises therein a cryogen inlet tube. The cryoprobe further comprises a cutting tip at the distal end of the housing and a cryogen vent adjacent to the proximal end and in fluid communication with the interior of the housing.

14 Claims, 2 Drawing Sheets

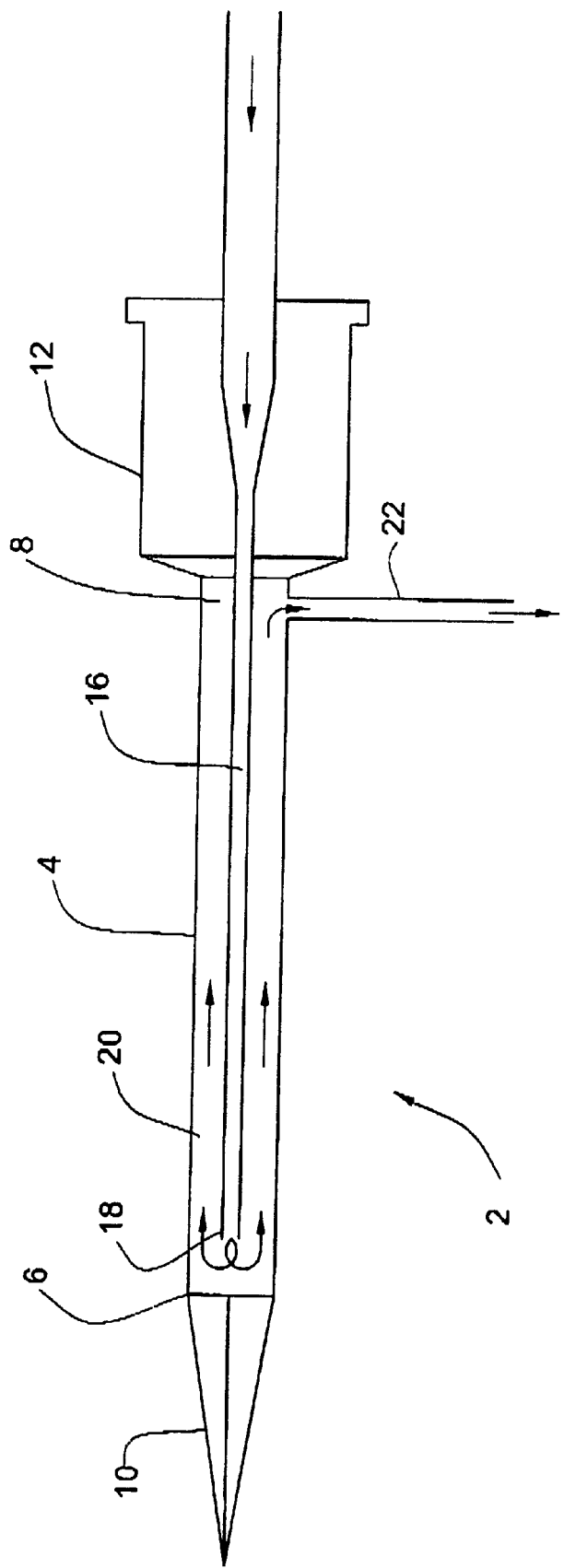
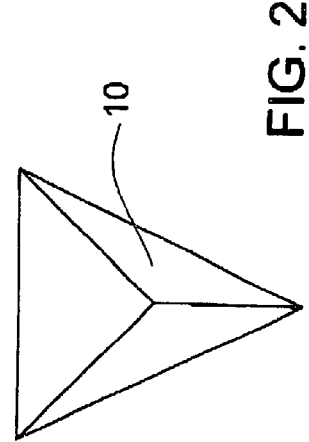
FIG. 1
FIG. 2

CRYOPROBE AND METHOD OF TREATING SCARS

FIELD OF THE INVENTION

This invention relates to a method for treating hypertrophic scars and keloids using a cryoprobe.

BACKGROUND OF THE INVENTION

Scar is the natural sequela of any wound and serves to impart strength through the elaboration and deposition of collagen into the dermis. A scar thus knits the wound together. However, the aesthetic appearance of a scar is generally unacceptable.

Certain regions of the body, including back, shoulders, sternum and earlobe, are especially prone to develop abnormal scars known as hypertrophic scars or keloids (at times referred to hereinafter collectively as keloids). These scars are bulky lesions representing an increased deposition of collagen fibers. They have the same clinical appearance: they are red, raised, and firm and posses a smooth, shiny surface. Whereas hypertrophic scars flatten spontaneously in the course of one to several years, keloids persist and extend beyond the site of the original injury. Patients suffering from hypertrophic scars or keloids complain about local pain, itchiness and local sensitivity, all of which compromise their quality of life as well as affect the individual body image.

The therapeutic management of these scars remains challenging. Treatment options include: silicone gel and silicone occlusive sheeting, compression therapy, intralesional corticosteroids or interferon, surface cryotherapy, radiotherapy, laser therapy and surgical excision.

Muti, E. and Ponzio, E. *Cryotherapy in the treatment of keloids,* Annals of Plastic Surgery (1983) 11:227–232, describes the treatment of keloids by placing a frozen cryoprobe on the lesion.

None of these treatment modalities are satisfying, since the recurrence rate is relatively high.

In recent years, methods and apparatus have been introduced in the cryosurgical field in order to treat cancerous masses inside the body (liver, brain, prostate and breast) and skin tumors.

U.S. Pat. No. 4,802,475 to Weshahy discloses a method of performing intralesional cryosurgery to treat benign, premalignant and malignant skin lesions. The treatment employs a bent hollow tubular needle having a front piercing surface coextensive with an opening and a back end adapted to receive a source of a cryogen gas. The needle is introduced into the skin from one point and runs at a depth below the lesion, exiting from the skin at another point beyond the lesion. The needle includes insulator material surrounding surface portions of the needle to define a thermally conducting non-insulated region for selectively freezing surrounding tissue. The cryogen flows through the needle, causing the non-insulated region of the needle to freeze surrounding tissue, the cryogen exiting from the protruding front opening of the needle.

U.S. Pat. No. 5,906,612 to Chinn discloses a cryosurgical probe and method for cryosurgically destroying cancer cells. A tissue dilator which has a sharp point at its front end and is surrounded by a removable, thermally insulating sheath or, alternatively, by a sheath having a heating element, is inserted through the patient's tissue to form an access channel to the cancerous tissue. The dilator is then removed leaving behind the sheath in the channel. Subsequently, a cryoprobe is inserted in the channel and an ice ball is formed at its distal end which extends beyond the insulating sheath.

U.S. Pat. No. 6,039,730 to Rabin et al discloses a cryoneedle having a pointed tip, a diameter less than 3.2 mm and a thermal insulation shell. The cryoneedle has within it two parallel, juxtaposed tubes, one for conveying the cryofluid to the tip and one for conveying the cryofluid from the tip to a vent.

SUMMARY OF THE INVENTION

It is an object of the invention to provide a novel cryoprobe.

It is a further object of the invention to provide a novel cryosurgical method for treating a hypertrophic scar or keloid.

In one aspect of the invention, there is provided a cryoprobe comprising an elongated, uninsulated housing having a sealed distal end and a proximal end, the housing comprising therein a cryogen inlet tube, the cryoprobe further comprising a cutting tip at the distal end of the housing and a cryogen vent adjacent to the proximal end and in fluid communication with the interior of the housing.

The cryoprobe of the invention is adapted to be inserted into a keloid in an intralesional cryosurgical treatment. Since the surface of the keloid is often hard, rubbery and dense, the cutting tip of the cryoprobe must be shaped so as to be capable of penetrating the surface. In one embodiment, the cutting tip is closed, that is, the tip comprises a plurality of cutting edges which come together at the extremity of the tip at one point. The cutting edges are sharp for smooth and controlled penetration and passage through the keloid. In a further embodiment, the cutting tip has a triangular cross section. The effective cutting edges are restricted to the front section of the needle and run into a triangulated body. In still further embodiments, the cutting tip may be spatulated, square shaped or diamond shaped. This differs from prior art cryoneedles, such as the one described in U.S. Pat. No. 4.802,475, which generally have an open tip. An open tip is generally not suitable for use in the method of the invention since it is difficult to insert into the keloid, causes trauma to the tissue and blood vessels, and allows tissue to penetrate the opening which may obstruct the flow of cryogen.

The housing of the cryoprobe has distal and proximal ends. The cutting tip is located at the distal end, while the proximal end is adapted for connection to a cryogen source. The housing is not enclosed by any thermal insulating sheath or heating element so as to maximize the tissue area which is frozen. The ice cylinder produced around the needle causes damage to the neighboring blood vessels as well as intra-and-extra-cellular biochemical, anatomical and physiological sequel which end in scar tissue anoxemia and ischemic necrosis. This enhances the involution of scar volume thereby reducing clinical and aesthetical complaints.

The housing of the cryoprobe of the invention is elongated and of reduced diameter so as to easily penetrate the opening in the keloid surface made by the cutting tip. A typical diameter of the cryoprobe housing is in the range of 1–4 mm. The housing is preferably rounded and straight (unbent) for ease of penetration. However, other shapes and forms of the housing are also possible.

The cryogen enters the housing from the proximal end through an inlet tube which is preferably of 0.4–0.8 mm diameter so as to provide sufficient cryogen to the housing. There may be more than one inlet tube inserted in the housing. The inlet tube has an outlet port at its distal end which is inserted into the housing to a location adjacent the distal end of the housing, which is sealed. A cryogen vent which is in fluid communication with the interior of the housing is positioned adjacent the proximal end of the housing. Thus, the liquid cryogen flows through the inlet tube to the distal end of the cryoprobe where it warms and becomes a gas. The gas then flows back to the proximal end of the housing through the space between the inlet tube and the housing and out through the vent. This ensures that the majority of the length of the cryoprobe is frozen.

In one embodiment, prior described below, the cryoprobe comprises a 22G needle (~0.6 mm diameter) inserted into a 14G needle (~1.6–1.7 mm diameter), the 22G needle serving as the inlet tube and the 14G needle serving as the housing. The 22G needle is 1 cm shorter than the 14G needle. It will be apparent to the skilled man of the art that other size combinations may be used, as long as they provide sufficient room for circulation of the cryogen liquid and gas and efficient cooling of the housing surface.

The cryogen may be any conventional cryofluid such as helium, argon or oxygen. Preferably, the cryogen is liquid nitrogen.

In a second aspect of the invention, there is provided an intralesional method for treating a hypertrophic scar or keloid using a cryoprobe comprising:

(a) inserting the cryoprobe into the hypertrophic scar or keloid so that the cryoprobe is positioned within the hypertrophic scar or keloid; and (b) introducing a cryogen into the cryoprobe thereby freezing the hypertrophic scar or keloid;

wherein the cryoprobe has a sealed distal end comprising a cutting tip.

In the method of the invention, the cryoprobe may be inserted into the keloid in a variety of ways such as obliquely, parallel or perpendicularly so as to maximize the freezing volume in the scar tissue. Since the cutting tip of the cryoprobe does not freeze, the tip may extend outside of the keloid on the side opposite the insertion point, although this is not required. The cryogen vent remains outside the keloid to vent the cryogen gas to the atmosphere. A number of cryoprobes may be used simultaneously to increase the treated volume. In such a configuration, the multiple cryoprobes may be connected to one or more cryogen sources.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 is a side sectional view of a cryoprobe according to one embodiment of the invention;

FIG. 2 is a perspective view of the tip of the cryoprobe of FIG. 1; and

DETAILED DESCRIPTION OF EMBODIMENTS

EXAMPLE 1

Figure 3:
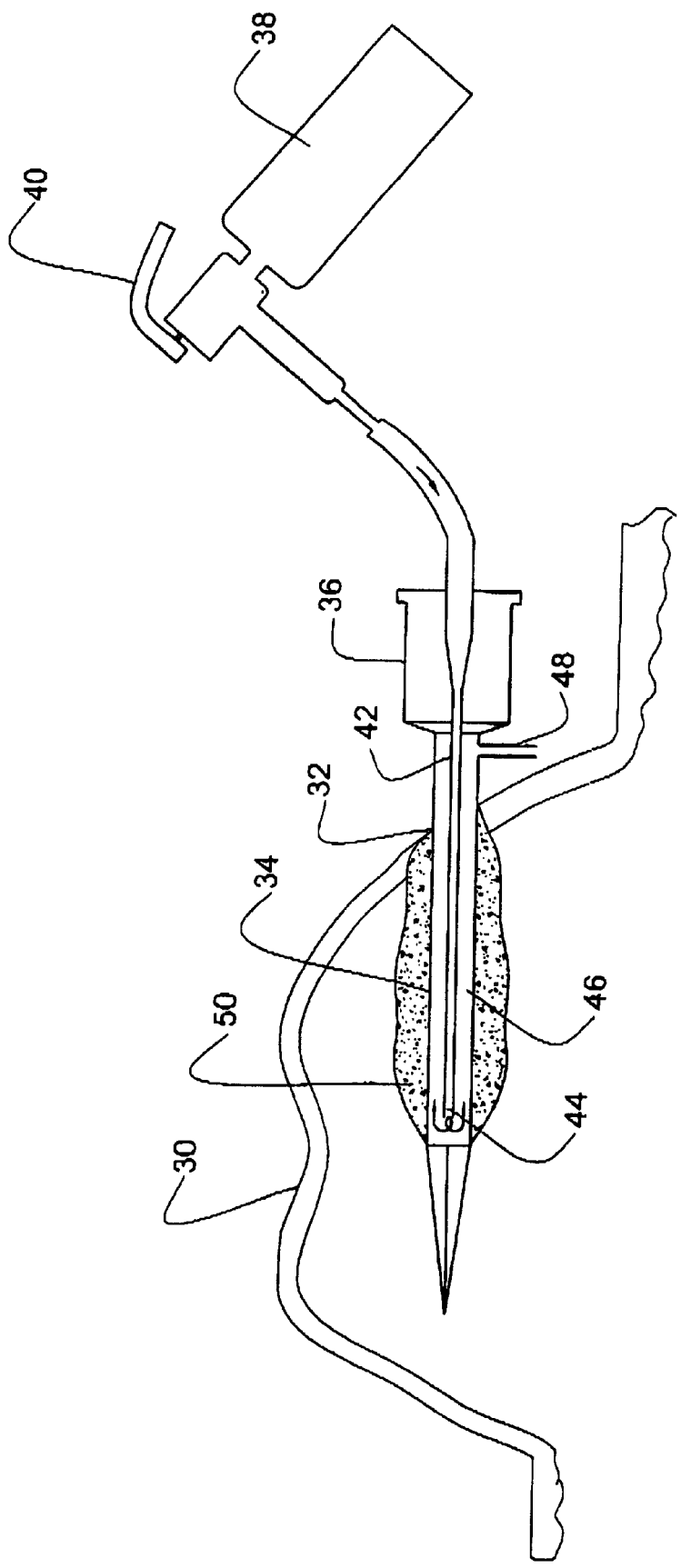
FIG. 3 is a side sectional view illustrating one embodiment of the method of the invention.

One embodiment of the cryoprobe of the invention is illustrated in FIG. 1. The cryoprobe, generally designated as 2, comprises an elongated, unbent housing 4 having a distal end 6 and a proximal end 8. The housing has no insulation surrounding it and has a cylindrical shape. A typical, non-limiting range of values for the length of the housing is 4–12 cm.

The distal end 6 of the housing is sealed by a cutting tip 10 which has a closed, triangular shape. The shape of the cutting tip is further illustrated in FIG. 2. This specially designed tip enables initial easy penetration into the hard, rubbery and dense composition of the scar. The effective cutting edge is restricted to the tip area of the cryoprobe. The proximal end 8 of the housing is blunt and has an adapter 12 attached thereto which may be connected to a cryogen source such as a cryogun containing liquid nitrogen gas.

The housing contains within it a cryogen inlet tube 16 which at its proximal end is connected to the adapter 12 and is capable of being in fluid communication with the cryogen source. An outlet port 18 is located at the distal end of the inlet tube 16 approximately 1–2 cm before the cutting tip. The interval between the outer surface of the inlet tube 16 and the inner surface of the housing 4 forms a space 20 into which the cryogen gas flows from the inlet tube. An example of a preferred diameter of this space is 0.5–1 mm. The cryogen gas exits through a vent 22 in fluid communication with the space 20 and located near the proximal end of the housing.

EXAMPLE 2

One embodiment of the method of the invention will now be described, with reference to FIG. 2.

The skin surface of the hypertrophic scar or keloid 30 is first cleansed with disinfectant solution. Then the penetrating area 32 into the scar is locally anesthetised with lidocaine. The sterile cryoprobe 34 is inserted trough the anesthetised area into the hypertrophic scar or keloid. The probe is preferably inserted into the long axis of the scar so as to maximize the volume of scar which is frozen. The cutting tip of the probe is preferably inserted into the scar tissue a few millimeters below the scar surface (epidermis) without penetrating the surrounding healthy tissue. The cryoprobe is then connected by the adapter 36 to a cryogun 38. The cryogun valve 40 is opened and the liquid nitrogen flows into the inlet tube 42 up to its distal outlet port 44 where it boils and becomes a gas. Thereafter, it enters the space 46 of the housing causing the wall of the housing to freeze. The cryogas is vented to the environment through the vent 48.

An ice cylinder 50 having a thickness of 1–3 mm forms around the cryoprobe, freezing the surrounding tissue. Cryotherapy is generally performed for approximately 3 minutes. After closing the valve, the cryoprobe defrosts and is withdrawn. The treatment may be repeated every 24 weeks until the scar is flattened.

Other modification of the invention will be apparent to the skilled man of the art. The scope of the invention, however, is to be defined by the following claims.

What is claimed is:

1. A cryoprobe comprising an elongated housing that is uninsulated along its entire length, having a sealed distal end and a proximal end, said housing comprising therein a cryogen inlet tube, said cryoprobe further comprising a cutting tip at the distal end of said housing and a cryogen vent abutting the proximal end and in fluid communication with the interior of said housing.

2. A cryoprobe according to claim 1 having a diameter of between approximately 1 and 4 mm.

3. A cryoprobe according to claim 1 wherein said cutting tip is closed.

4. A cryoprobe according to claim 1 wherein said cutting tip has a triangular blade cross section.

5. A cryoprobe according to claim 1 wherein said cutting tip is diamond shaped.

6. A cryoprobe according to claim 1 wherein said housing is substantially unbent.

7. A cryoprobe according to claim 1 wherein said proximal end is adapted to be connected to a cryogen source.

8. A cryoprobe according to claim 1 wherein said cryogen inlet tube has an outlet port at one end and said outlet port is located adjacent to said distal end of said housing.

9. An intralesional method for treating a hypertrophic scar or keloid using the cryoprobe of claim 1 comprising:
   a) inserting said cryoprobe into said hypertrophic scar or keloid so that the cryoprobe is positioned within said hypertrophic scar or keloid; and
   b) introducing a cryogen into said cryoprobe thereby freezing said hypertrophic scar or keloid;
wherein said cryoprobe has a sealed distal end comprising a cutting tip.

10. A method according to claim 9 wherein said cryoprobe comprises a cryogen inlet tube.

11. A method according to claim 10 wherein said cryogen inlet tube has an outlet port at one end and said outlet port is located adjacent to the distal end of said cryoprobe.

12. A method according to claim 9 wherein said cryoprobe comprises a vent in fluid communication with the interior of said cryoprobe.

13. A method according to claim 9 further comprising the step of allowing the cryoprobe to defrost and subsequently withdrawing the cryoprobe from the hypertrophic scar or keloid.

14. A method according to claim 9 wherein said cryogen is liquid nitrogen.

* * * * *